US011092587B2

(12) United States Patent
Nakatani et al.

(10) Patent No.: US 11,092,587 B2
(45) Date of Patent: Aug. 17, 2021

(54) METHOD FOR EVALUATING CELLULOSE NANOFIBER DISPERSION

(71) Applicant: NIPPON PAPER INDUSTRIES CO., LTD., Tokyo (JP)

(72) Inventors: Takeshi Nakatani, Yamaguchi (JP); Shinji Sato, Yamaguchi (JP); Koji Kimura, Yamaguchi (JP)

(73) Assignee: NIPPON PAPER INDUSTRIES CO., LTD., Tokyo (JP)

( * ) Notice: Subject to any disclaimer, the term of this patent is extended or adjusted under 35 U.S.C. 154(b) by 33 days.

(21) Appl. No.: 15/550,882

(22) PCT Filed: Feb. 16, 2016

(86) PCT No.: PCT/JP2016/054416
§ 371 (c)(1),
(2) Date: Aug. 14, 2017

(87) PCT Pub. No.: WO2016/133076
PCT Pub. Date: Aug. 25, 2016

(65) Prior Publication Data
US 2018/0045706 A1    Feb. 15, 2018

(30) Foreign Application Priority Data

Feb. 17, 2015  (JP) .............................. JP2015-028609

(51) Int. Cl.
| | | |
|---|---|---|
| *G01N 33/36* | (2006.01) | |
| *C08J 3/03* | (2006.01) | |
| *C08J 3/05* | (2006.01) | |
| *G01N 33/34* | (2006.01) | |
| *G01N 15/02* | (2006.01) | |
| *G01N 15/14* | (2006.01) | |
| *C08L 1/02* | (2006.01) | |
| *C08J 3/09* | (2006.01) | |
| *C08J 3/215* | (2006.01) | |
| *D21H 11/18* | (2006.01) | |
| *D21H 11/20* | (2006.01) | |
| *D21H 17/67* | (2006.01) | |
| *G01N 1/38* | (2006.01) | |
| *G02B 21/34* | (2006.01) | |
| *G01N 15/00* | (2006.01) | |

(52) U.S. Cl.
CPC ............... *G01N 33/36* (2013.01); *C08J 3/03* (2013.01); *C08J 3/05* (2013.01); *C08J 3/09* (2013.01); *C08J 3/215* (2013.01); *C08L 1/02* (2013.01); *D21H 11/18* (2013.01); *D21H 11/20* (2013.01); *D21H 17/67* (2013.01); *G01N 1/38* (2013.01); *G01N 15/0227* (2013.01); *G01N 15/1463* (2013.01); *G01N 33/343* (2013.01); *G02B 21/34* (2013.01); *C08J 2301/02* (2013.01); *G01N 2015/0053* (2013.01); *G01N 2015/0092* (2013.01); *G01N 2015/1493* (2013.01)

(58) Field of Classification Search
CPC .. G01N 33/36; G01N 33/00; C08J 3/03; C08J 3/05; C08J 3/09; C08J 3/00
USPC .......................................................... 436/164
See application file for complete search history.

(56) References Cited

U.S. PATENT DOCUMENTS

| | | | | |
|---|---|---|---|---|
| 2006/0019409 | A1* | 1/2006 | Nelson | ............... G06K 9/00127 436/524 |
| 2010/0254961 | A1* | 10/2010 | Nishio | ..................... A61K 8/64 424/94.1 |

FOREIGN PATENT DOCUMENTS

| | | |
|---|---|---|
| EP | 2226171 A1 | 9/2010 |
| JP | 2005305724 A | 11/2005 |
| JP | 2006-008857 A | 1/2006 |
| JP | 2013-181167 A | 9/2013 |
| JP | 2014092551 A | 5/2014 |
| JP | 2014114332 A | 6/2014 |
| JP | 2014-125691 A | 7/2014 |
| JP | 2014-136775 A | 7/2014 |
| JP | 2014141658 A | 8/2014 |
| JP | 2014193959 A | 10/2014 |

OTHER PUBLICATIONS

Kawanishi M, JP2014092551 English Machine Translation of Description, obtained on Feb. 14, 2019, May 19, 2014, pp. 1-57. (Year: 2014).*
Takeshi et al, JP 2014-092551 English Machine Translation, Optical Film and Manufacturing Method Therefor, obtained on Apr. 24, 2019, pp. 1-62. (Year: 2019).*
Yosuke et al, JP 2013-181167 English Machine Translation, Aqueous Ink Composition and Writing Instrument Using the Same, obtained on Apr. 25, 2019, pp. 1-56. (Year: 2019).*
Khatri, Pad dyeing of cellulose acetate nanofibres with disperse dyes, Color. Technology., 129, 2012, 159-163. (Year: 2012).*
Tyson, A quantitative method for analyzing the dispersion and agglomerationof nano-particles in composite materials, Composites: Part B, 42, (2011), 1395-1403. (Year: 2011).*
Goi, English Machine Translation of JP 2013-181167 A1 Description, obtained form https://worldwide.espacenet.com/singleLineSearch?locale=en_EP on Nov. 4, 2020, pp. 1-60. (Year: 2020).*

(Continued)

*Primary Examiner* — Christine T Mui
(74) *Attorney, Agent, or Firm* — McCarter & English, LLP; Steven G. Davis; Wei Song

(57) ABSTRACT

Herein provided are methods for evaluating cellulose nanofiber dispersions, comprising the steps of: (1) preparing a cellulose nanofiber dispersion; (2) adding a color material into the cellulose nanofiber dispersion; and (3) observing the cellulose nanofiber dispersion to which a colored pigment has been added with a light microscope. The methods allow for easy evaluation of whether or not agglomerates of cellulose nanofibers exist in cellulose nanofiber dispersions, which cannot be visually determined.

5 Claims, 3 Drawing Sheets

(56) References Cited

OTHER PUBLICATIONS

Supplementary European Search Report for Application No. 16752462.8, dated Jan. 4, 2019, 9 pages.
Navarro et al., Labelling of N-hydroxysuccinimide-modified rhodamine B on cellulose nanofibrils by the amidation reaction. RSC Advances. 2014; 4(105):60757-61.
Supplementary Partial European Search Report for Application No. 16752462.8, dated Oct. 5, 2018, 9 pages.
Supplementary European Search Report for Application No. 16752462.8, dated Sep. 5, 2019, 12 pages.
Nichols et al., A review of the terms agglomerate and aggregate with a recommendation for nomenclature used in powder and particle characterization. J Pharm Sci. Oct. 2002;91(10):2103-9.

* cited by examiner

METHOD FOR EVALUATING CELLULOSE NANOFIBER DISPERSION

CROSS-REFERENCE TO RELATED APPLICATIONS

This application is a U.S. national stage filing, under 35 U.S.C. § 371(c), of International Application No. PCT/JP2016/054416, filed on Feb. 16, 2016, which claims priority to Japanese Patent Application No. 2015-028609, filed on Feb. 17, 2015. The entire contents of each of the aforementioned applications are incorporated herein by reference.

TECHNICAL FIELD

The present invention relates to methods for evaluating cellulose nanofiber dispersions.

BACKGROUND ART

Cellulose nanofibers (CNFs) are fine fibers having a fiber diameter in the order of about 4 to several hundred nanometers with high dispersity in water-based media so that they are expected to be applied as reinforcing materials for resins; for maintaining the viscosity of foods, cosmetics, medical products or coatings or the like; for strengthening doughs as precursors of foodstuffs and holding water in them; for improving food stability; and as low-calorie additives or emulsion stabilizing aids (patent document 1 and the like). In cases where CNFs are used as additives, they are typically used in a dispersed state in water (i.e., in a wet state).

CITATION LIST

Patent Literature

Patent document 1: JPA No. 2008-1728.

SUMMARY OF INVENTION

Technical Problem

CNFs are expected to be applied for various purposes, but CNFs may associate with each other to form agglomerates in CNF dispersions, thus inviting various problems. Therefore, it should be necessary to ascertain whether or not agglomerates exist in CNF dispersions in advance, and to remove or disintegrate any possible agglomerates in the CNF dispersions as appropriate. However, CNFs are very thin fibers so that their dispersions are highly transparent, which caused the problem that agglomerates of CNFs could not be visually identified if they existed.

Under these circumstances, the present invention aims to provide methods for evaluating whether or not agglomerates of CNFs exist in CNF dispersions, which cannot be visually determined.

Technical Problem

[1] A method for evaluating a cellulose nanofiber dispersion, comprising the steps of:
(1) preparing a cellulose nanofiber dispersion;
(2) adding a color material into the cellulose nanofiber dispersion; and
(3) observing the cellulose nanofiber dispersion to which the color material has been added with a light microscope.

[2] The method of [1], wherein the color material is a colored pigment.

[3] The method of [2], wherein the colored pigment has an average particle size of 10 μm or less.

[4] The method of any one of [1] to [3], wherein the step (2) comprises adding a dispersion of a colored pigment to the cellulose nanofiber dispersion.

[5] The method of any one of [1] to [4], further comprising the step of:
(4) determining the CNF dispersion index as follows:
1) sandwich the dispersion between two glass plates to form a film having a thickness of 0.15 mm; observe the film with a microscope to measure the major axes of agglomerates; and classify the agglomerates as follows:
agglomerates having a size of 100 to 150 μm: large particles; agglomerates having a size of 50 to 100 μm: medium-sized particles; agglomerates having a size of 20 to 50 μm: small particles; and
2) calculate the CNF dispersion index by the equation below:

CNF dispersion index=(the number of large particles×64+the number of medium-sized particles×8+the number of small particles×1)÷2.

[6] A cellulose nanofiber dispersion containing no agglomerates having a size of 150 μm or more as evaluated by the method of any one of [1] to [4].

[7] A cellulose nanofiber dispersion having a CNF dispersion index of 500 or less as determined by the method defined in [5].

[8] The cellulose nanofiber dispersion of [6] or [7], which is a dispersion obtained by drying a cellulose nanofiber dispersion once prepared and then redispersing it in a dispersion medium.

[9] A food containing the cellulose nanofiber dispersion of any one of [6] to [8] or a cellulose nanofiber from the dispersion.

[10] A cosmetic containing the cellulose nanofiber dispersion of any one of [6] to [8] or a cellulose nanofiber from the dispersion.

[11] A rubber composition containing the cellulose nanofiber dispersion of any one of [6] to [8] or a cellulose nanofiber from the dispersion.

Advantageous Effects of Invention

The present invention makes it possible to provide methods for evaluating whether or not agglomerates of CNFs exist in CNF dispersions, which cannot be visually determined.

DESCRIPTION OF EMBODIMENTS

Figure 1:
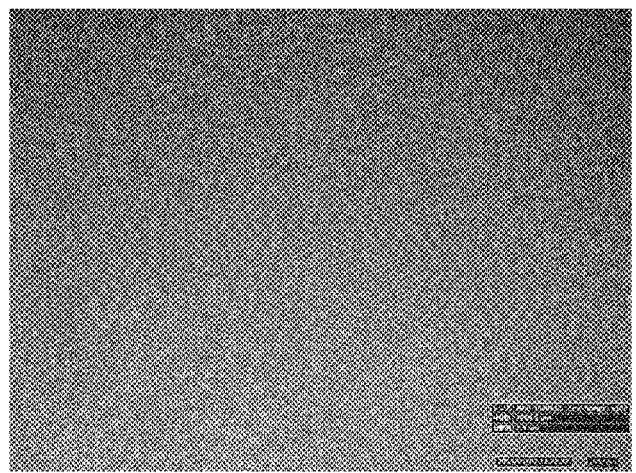
FIG. 1 shows an image of the CNF dispersion in Example 1 observed with a light micro scope.

The methods for evaluating cellulose nanofiber (CNF) dispersions according to the present invention comprise the steps of: (1) preparing a dispersion of a cellulose nanofiber; (2) adding a color material into the cellulose nanofiber dispersion; and (3) observing the cellulose nanofiber dispersion to which the color material has been added with a light microscope. As used herein, the range "A to B" includes its endpoint values, i.e., A and B. The expression "A or B" includes either one or both of A and B.

As used herein, the term "agglomerates of cellulose nanofibers (CNFs)" refers to poorly disintegrated fibers produced during the disintegration process described later, CNF network structures produced in dispersions, or agglomerates produced during the concentration or drying of CNFs or the like. These agglomerates contain the dispersion media of the dispersions within them so that they are highly transparent in the visible region and cannot be visually identified.

(Cellulose Nanofibers)

Cellulose nanofibers (CNFs) are fine fibers having a fiber width of about 4 to 500 nm and an aspect ratio of 100 or more that can be obtained by disintegrating cellulose fibers having undergone a chemical treatment such as cationization or anionization. Anionization treatments include carboxylation (i.e., oxidization), carboxymethylation, esterification, functionalization and the like.

(Cellulose Base Materials)

Cellulose base materials for preparing chemically modified cellulose include, for example, those derived from plant materials (e.g., wood, bamboo, hemp, jute, kenaf, farm wastes, cloth, pulp), animal materials (e.g., Ascidiacea), algae, products produced by microorganisms (e.g., acetic acid bacteria (Acetobacter)), and the like. Pulps include softwood unbleached kraft pulp (NUKP), softwood bleached kraft pulp (NBKP), hardwood unbleached kraft pulp (LUKP), hardwood bleached kraft pulp (LBKP), softwood unbleached sulfite pulp (NUSP), softwood bleached sulfite pulp (NBSP), thermomechanical pulp (TMP), recycled pulp, waste paper pulp, and the like. Any of these materials can be used, but cellulose fibers derived from plants or microorganisms are preferred, among which cellulose fibers derived from plants are more preferred.

(Carboxymethylation)

When a carboxymethylated cellulose is used as a chemically modified cellulose in the present invention, the carboxymethylated cellulose may be obtained by carboxymethylating any one of the cellulose base materials listed above by a known method, or may be commercially available. In either case, the degree of carboxymethyl substitution per anhydrous glucose unit of the cellulose is preferably 0.01 to 0.50. An example of a process for preparing such a carboxymethylated cellulose is as follows. A cellulose is used as a starting material in a solvent consisting of water or a lower alcohol in an amount of 3 to 20 times the mass of the cellulose. Specifically, water, methanol, ethanol, N-propyl alcohol, isopropyl alcohol, N-butanol, isobutanol, tert-butanol or the like can be used alone or as a combination of two or more of them. When a mixed solvent of water and a lower alcohol is used, the proportion of the lower alcohol is 60 to 95% by mass. A mercerizing agent consisting of an alkali metal hydroxide such as sodium hydroxide or potassium hydroxide is used in an amount of 0.5 to 20 molar equivalents per anhydrous glucose residue of the starting material. The starting material, solvent, and mercerizing agent are mixed to perform a mercerization process at a reaction temperature 0 to 70° C., preferably 10 to 60° C. for a reaction period of 15 minutes to 8 hours, preferably 30 minutes to 7 hours. Then, a carboxymethylating agent is added in an amount of 0.05 to 10.0 molar equivalents per glucose residue to perform an etherification reaction at a reaction temperature of 30 to 90° C., preferably 40 to 80° C. for a reaction period of 30 minutes to 10 hours, preferably 1 hour to 4 hours.

(Carboxylation)

When a carboxylated (oxidized) cellulose is used as a chemically modified cellulose in the present invention, the carboxylated cellulose (also referred to as "oxidized cellulose") can be obtained by carboxylating (oxidizing) any one of the cellulose base materials by a known method. The carboxyl group content is preferably, but not limited to, 0.6 to 2.0 mmol/g, more preferably 1.0 mmol/g to 2.0 mmol/g based on the bone dry mass of the anionically modified cellulose nanofibers.

An example of a carboxylation (oxidation) method comprises oxidizing a cellulose base material using an oxidizing agent in water in the presence of a compound selected from the group consisting of an N-oxyl compound, a bromide, an iodide and a mixture thereof. This oxidation reaction allows the primary hydroxyl group at the C6 position of the glucopyranose ring on the surface of the cellulose to be selectively oxidized to give cellulose fibers having an aldehyde group and a carboxyl group (—COOH) or a carboxylate group (—COO⁻) on their surface. During the reaction, the concentration of the cellulose is not specifically limited, but preferably 5% by mass or less.

The term "N-oxyl compound" refers to a compound capable of generating nitroxyl radicals. Any N-oxyl compounds can be used so far as they promote the intended oxidation reaction. Examples include 2,2,6,6-tetramethylpiperidin-1-oxy radical (TEMPO) and derivatives thereof (e.g., 4-hydroxy-TEMPO).

The amount of the N-oxyl compound used is not specifically limited so far as it is a catalytic amount enough to oxidize the cellulose used as a base material. For example, it is preferably 0.01 to 10 mmol, more preferably 0.01 to 1 mmol, still more preferably 0.05 to 0.5 mmol per gram of bone dry cellulose. It is also preferably about 0.1 to 4 mmol/L of the reaction system.

The term "bromide" refers to a compound containing bromine, examples of which include alkali metal bromides that can be ionized by dissociation in water. Similarly, the term "iodide" refers to a compound containing iodine, examples of which include alkali metal iodides. The amount of the bromide or iodide used can be selected in a range that can promote the oxidation reaction. The total amount of the bromide and iodide is preferably, for example, 0.1 to 100 mmol, more preferably 0.1 to 10 mmol, still more preferably 0.5 to 5 mmol per gram of bone dry cellulose.

Any known oxidizing agents can be used, including, for example, halogens, hypohalous acids, halous acids, perhalogenic acids or salts thereof, halogen oxides, peroxides and the like. Among others, sodium hypochlorite is preferred because it is inexpensive and less environmentally harmful. The amount of the oxidizing agent used is preferably 0.5 to 500 mmol, more preferably 0.5 to 50 mmol, still more preferably 1 to 25 mmol, most preferably 3 to 10 mmol per gram of bone dry cellulose, for example. It is also preferably 1 to 40 mol per mole of the N-oxyl compound.

During the oxidation process of the cellulose, the reaction efficiently proceeds even under relatively mild conditions. Thus, the reaction temperature is preferably 4 to 40° C., or may be room temperature around 15 to 30° C. As the reaction proceeds, the pH of the reaction solution is found to decrease because carboxyl groups are generated in the cellulose. To ensure that the oxidation reaction efficiently proceeds, an alkaline solution such as an aqueous sodium hydroxide solution is preferably added to maintain the pH of the reaction solution in the order of 8 to 12, preferably 10 to 11. The reaction medium is preferably water because of easy handling, low likelihood of side reactions and the like.

The reaction period in the oxidation reaction can be appropriately selected depending on the extent to which oxidation proceeds, typically in the order of 0.5 to 6 hours, for example 0.5 to 4 hours.

In addition, the oxidation reaction may be performed in two stages. For example, the oxidized cellulose obtained by filtration after the end of a first stage reaction can be oxidized again under the same or different reaction conditions, whereby the reaction is not inhibited by the salt produced as a by-product during the first stage reaction and efficient oxidation can be achieved.

Another example of a carboxylation (oxidation) method may comprise contacting a cellulose base material with an ozone-containing gas. This oxidation reaction allows hydroxyl groups at least at the 2- and 6-positions of the glucopyranose ring to be oxidized and cellulose chains to be cleaved. The ozone concentration in the ozone-containing gas is preferably 50 to 250 $g/m^3$, more preferably 50 to 220 $g/m^3$. The amount of ozone added to the cellulose base material is preferably 0.1 to 30 parts by mass, more preferably 5 to 30 parts by mass per 100 parts by mass of the cellulose base material on a solids basis. The ozonation temperature is preferably 0 to 50° C., more preferably 20 to 50° C. The ozonation period is not specifically limited, but in the order of 1 to 360 minutes, preferably 30 to 360 minutes. If the ozonation conditions are within these ranges, the cellulose can be prevented from being excessively oxidized and cleaved, thereby improving the yield of the oxidized cellulose. The ozonation may be followed by a post-oxidation process using an oxidizing agent. The oxidizing agent used in the post-oxidation process is not specifically limited, but may include chlorine compounds such as chlorine dioxide and sodium chlorite; as well as oxygen, hydrogen peroxide, persulfuric acid, peracetic acid and the like. For example, the post-oxidation process can be performed by dissolving one of these oxidizing agents in water or a polar organic solvent such as an alcohol to prepare a solution of the oxidizing agent and immersing the cellulose base material in the solution.

The carboxyl group content of the oxidized cellulose can be adjusted by controlling the reaction conditions described above such as the amount of the oxidizing agent added, the reaction period and the like.

(Cationization) When a cationized cellulose is used as a chemically modified cellulose in the present invention, the cationically modified cellulose can be obtained by reacting any one of the cellulose base materials with a cationizing agent such as glycidyltrimethylammonium chloride, 3-chloro-2-hydroxypropyltrialkylammonium hydride or a halohydrin form thereof and an alkali metal hydroxide (sodium hydroxide, potassium hydroxide or the like) as a catalyst in the presence of water or an alcohol containing 1 to 4 carbon atoms. In this process, the degree of cationic substitution per glucose unit of the resulting cationically modified cellulose can be adjusted by controlling the amount of the reactant cationizing agent added or the proportion of water and the alcohol if they are used as a mixed solvent.

The degree of cationic substitution of the cationically modified cellulose is preferably 0.02 to 0.50 per glucose unit. When a cationic substituent is introduced into cellulose fibers, the cellulose fibers electrically repel each other. Therefore, the cellulose fibers into which a cationic substituent has been introduced can be readily disintegrated into nanofibers. If the degree of cationic substitution is lower than 0.02 per glucose unit, they cannot be sufficiently disintegrated into nanofibers. If the degree of cationic substitution is higher than 0.50 per glucose unit, however, they may be swollen or dissolved and may fail to form nanofibers. For efficient disintegration, the cationized cellulosic base material obtained as described above is preferably washed.

(Esterification)

An esterified cellulose can also be used as a chemically modified cellulose. Esterification may take place by mixing a cellulose base material with a powder or an aqueous solution of phosphate-based compound A; or adding an aqueous solution of phosphate-based compound A to a slurry of a cellulose base material, or the like. Examples of phosphate-based compound A include phosphoric acid, polyphosphoric acid, phosphorous acid, phosphonic acid, polyphosphonic acid or esters thereof. These may be in the form of a salt. Among these examples, phosphate group-containing compounds are preferred because they are inexpensive and easy to handle and the disintegration efficiency can be improved by introducing a phosphate group into cellulose pulp fibers. Phosphate group-containing compounds include phosphoric acid, sodium dihydrogen phosphate, disodium hydrogen phosphate, trisodium phosphate, sodium pyrophosphate, sodium metaphosphate, potassium dihydrogen phosphate, dipotassium hydrogen phosphate, tripotassium phosphate, potassium pyrophosphate, potassium metaphosphate, ammonium dihydrogen phosphate, diammonium hydrogen phosphate, triammonium phosphate, ammonium pyrophosphate, ammonium metaphosphate, and the like. These can be used alone or as a combination of two or more of them. Among them, phosphoric acid, sodium salts of phosphoric acid, potassium salts of phosphoric acid, and ammonium salts of phosphoric acid are preferred because phosphate groups are introduced efficiently, disintegration is promoted in the disintegration process described below and they are readily industrially applied, and specifically, sodium dihydrogen phosphate and disodium hydrogen phosphate are more preferred. Further, the phosphate-based compound A is desirably used as an aqueous solution because the reaction can proceed uniformly and phosphate groups are introduced more efficiently. The pH of the aqueous solution of the phosphate-based compound A is preferably 7 or less to introduce phosphate groups more efficiently, whereas the pH is preferably 3 to 7 to reduce the hydrolysis of pulp fibers.

An example of a process for preparing a cellulose phosphate ester is as follows: To a suspension of a cellulose base material having a solids content of 0.1 to 10% by weight is added phosphate-based compound A with stirring to introduce a phosphate group into the cellulose. The amount of the phosphate-based compound A added is preferably 0.2 to 500 parts by weight, more preferably 1 to 400 parts by weight expressed as the amount of elemental phosphorus per 100 parts by weight of the cellulose base material. If the proportion of the phosphate-based compound A is equal to or higher than the lower limit indicated above, the yield of microfibrous cellulose can be further improved. However, it is not preferable in terms of costs to exceed the upper limit indicated above because the yield cannot be further improved.

In addition to the phosphate-based compound A, a powder or an aqueous solution of compound B may be mixed. The compound B is not specifically limited, but preferably a basic nitrogen-containing compound. The term "basic" as used here is defined to mean that the compound in aqueous solution turns pink-red in the presence of the phenolphthalein indicator or the compound in aqueous solution has a pH of more than 7. The basic nitrogen-containing compound used in the present invention is not limited so far as the advantages of the present invention are achieved, but it is preferably an amino-containing compound. Such compounds include urea, methylamine, ethylamine, trimethylamine, triethylamine, monoethanolamine, diethanolamine, triethanolamine, pyridine, ethylene diamine, hexamethylene diamine and the like. Among others, urea is preferred because it is inexpensive and excellent in handling. The amount of compound B added is preferably 2 to 1000 parts by weight, more preferably 100 to 700 parts by weight per 100 parts by weight of the cellulose base material on a solids basis. The reaction temperature is preferably 0 to 95° C., more preferably 30 to 90° C. The reaction period is not specifically limited, but about 1 to 600 minutes, more preferably 30 to 480 minutes. If the esterification reaction conditions are within these ranges, the cellulose can be prevented from being excessively esterified and readily dissolved, thereby improving the yield of the cellulose phosphate ester. After the resulting cellulose phosphate ester suspension is dehydrated, it is preferably heated at 100 to 170° C. to reduce the hydrolysis of the cellulose. Further, it is heated at 130° C. or less, preferably 110° C. or less while water is contained during the heat treatment, and after water has been removed, it is preferably heated at 100 to 170° C.

Preferably, the degree of phosphate substitution of the cellulose phosphate ester is 0.001 to 0.40 per glucose unit. When a phosphate substituent is introduced into cellulose fibers, the cellulose fibers electrically repel each other. Therefore, the cellulose fibers into which a phosphate group has been introduced can be readily disintegrated into nanofibers. If the degree of phosphate substitution is lower than 0.001 per glucose unit, they cannot be sufficiently disintegrated into nanofibers. If the degree of phosphate substitution is higher than 0.40 per glucose unit, however, they may be swollen or dissolved and may fail to form nanofibers. For efficient disintegration, the cellulosic base material esterified by phosphate groups obtained as described above is preferably boiled and then washed with cold water.

(Color Materials)

The term "color material" refers to a material having a color such as white, black, blue, red, yellow, green or the like. In the present invention, a colored pigment or a dye can be used as a color material.

(Colored Pigments)

As used herein, the term "colored pigment" refers to a pigment having a color such as white, black, blue, red, yellow, green or the like in any particle shapes including, but not specifically limited to, plate-like, spherical, flaky and other particles. Colored pigments include inorganic pigments and organic pigments. Examples of inorganic pigments include carbon black, black iron oxide, black complex metal oxides, zinc chromate, lead chromate, red lead, zinc phosphate, vanadium phosphate, calcium phosphate, aluminum phosphomolybdate, calcium molybdate, aluminum tripolyphosphate, bismuth oxide, bismuth hydroxide, basic bismuth carbonate, bismuth nitrate, bismuth silicate, hydrotalcite, zinc dust, micaceous iron oxide, calcium carbonate, barium sulfate, alumina white, silica, diatomaceous earth, kaolin, talc, clay, mica, barium oxide, organic bentonite, white carbon, titanium oxide, zinc oxide, antimony oxide, lithopone, white lead, perylene black, molybdenum red, cadmium red, red iron oxide, cerium sulfide, chrome yellow, cadmium yellow, yellow iron oxide, yellow ochre, bismuth yellow, sienna, amber, green earth, Mars Violet, ultramarine blue, Prussian blue, basic lead sulfate, basic lead silicate, zinc sulfide, antimony trioxide, calcium complexes, phthalocyanine blue, phthalocyanine green, ochre, aluminum powder, copper powder, brass powder, stainless steel powder, titanium oxide-coated mica, iron oxide-coated mica, copper zinc oxide, silver particles, anatase titanium oxide, iron oxide-based calcined pigments, conductive metal powder, microwave-absorbing ferrites and the like. Organic pigments include Quinacridone Red, Polyazo Yellow, Anthraquinone Red, Anthraquinone Yellow, Polyazo Red, Azo Lake Yellow, Perylene, Phthalocyanine Blue, Phthalocyanine Green, Isoindolinone Yellow, Watching Red, Permanent Red, Para Red, Toluidine Maroon, Benzidine Yellow, Fast Sky Blue, Brilliant Carmine 6B and the like. These pigments can be used alone or as a combination of two or more of them.

The colored pigments have an average particle size of 10 µm or less, preferably 0.01 or more and 10 µm or less, more preferably 0.03 or more and 1 µm or less. If the average particle size is 10 µm or less, preferably 1 µm or less, evaluation will be easier because the dispersity of colored pigments in CNF dispersions becomes stable. On the other hand, the lower limit is not limited, but if the average particle size is smaller than 0.01 µm, agglomerates may be difficult to observe with a light microscope because colored pigments may infiltrate into the agglomerates. The average particle size is measured by a laser diffraction particle size distribution analyzer (e.g., Mastersizer 3000 or Zetasizer Nano ZS from Malvern). In the case of non-spherical pigments, the average of the major axis lengths is taken as the average particle size.

(Dyes)

The term "dye" refers to an organic colorant which selectively absorbs or reflects visible light to exhibit its own color and with which fibers, pigments and the like are stained by an appropriate staining method. Dyes include azo dyes, diphenyl- and triphenylmethane dyes, azine dyes, oxazine dyes, thiazine dyes and the like. These dyes may be used alone or as a combination of two or more of them.

(Pigment Dispersions)

In the present invention, a colored pigment dispersion containing a colored pigment stably dispersed in a water-based solvent using a dispersant or the likes is preferably added to the CNF dispersion. The use of the colored pigment dispersion helps make observation with a light microscope easier.

Such water-based solvents include water, methanol, ethanol, N-propyl alcohol, isopropyl alcohol, N-butanol, isobutanol, tertiary butanol, linear or branched pentanediol, aliphatic ketones (e.g., acetone, methyl ethyl ketone, diacetone alcohol, etc.), polyols (e.g., ethylene glycol, diethylene glycol, triethylene glycol, etc.), polyglycols having a molar mass of 200 to 2000 g/mol, propylene glycol, dipropylene glycol, tripropylene glycol, trimethylolpropane, glycerol, thiodiglycol, 2-pyrrolidone, N-methylpyrrolidone, N-ethylpyrrolidone, 1,3-dimethylimidazolidinone, dimethylacetamide, dimethylformamide, and combinations thereof.

Dispersants include higher fatty acids, higher fatty acid amides, metallic soaps, glycerin esters, hydrotalcite, polyethylene waxes, polypropylene waxes, glue, gelatin and the like, alone or as a combination of two or more of them.

The amount of the colored pigment in the colored pigment dispersion is not limited, but preferably about 5 to 20% by mass. If the amount of the colored pigment contained is low, the photographs taken through a light microscope look pale, but if the amount of the colored pigment contained is high, agglomerates of the colored pigment may be generated.

In the present invention, preferred colored pigments are those providing a high contrast and less transparent to light (i.e., highly absorptive to light) during observation with a light microscope, among which black pigments are more preferred. Further, they preferably resist secondary agglomeration or agglomeration due to interaction with CNFs during observation. For example, colored pigment dispersions that can be used include predispersed liquid sumi inks for brush calligraphy and paintings including those available under the brand name Bokuteki, pigment inks for inkjet printers and the like. Sumi is surface-treated carbon black coated with a water-based resin on the surface and shows high dispersity and resists secondary agglomeration when it is mixed with a binder resin so that it achieves sufficiently high blackness even in CNF dispersions at relatively low concentrations. Predispersed liquid sumi inks including those available under the brand name Bokuteki are water-based dispersions containing surface-treated carbon black and they are prepared by, for example, coating the surface of amorphous furnace black made by the furnace process involving incomplete combustion of a petroleum- or coal-derived oil in a high-temperature gas or the like with a water-based resin, adding a glycol-based anti-freezing agent and a preservative as appropriate, mixing them and slurring the mixture. In the present invention, commercially available products (e.g., those available under the brand name "Bokuteki" from Kuretake Co., Ltd. and the like) can be used. Surface-treated carbon black or water-based dispersions thereof can also be prepared according to known methods (e.g., JPA No. 1995-188597 or JPA No. 1994-234946). Predispersed liquid sumi inks including those available under the brand name Bokuteki, and pigment inks for inkjet printers may be used alone or as a combination of two or more of them.

(Observation with a Light Microscope)

In the present invention, the concentration of the CNF dispersion is not specifically limited, but preferably about 0.01 to 10% by mass, more preferably about 0.1 to 2% by mass. If the concentration is low, the amount of agglomerates decreases, but if the concentration is high, the viscosity increases to make it difficult to disperse the colored pigment, whereby the precision decreases in either case.

In the present invention, the light microscope with which the cellulose nanofiber dispersion containing a color material is observed is not specifically limited, and any conventional light microscopes (including digital microscopes) can be used. The magnification at which the CNF dispersion is observed with the light microscope is not limited, but preferably 50 to 1000 times.

In the present invention, CNF dispersions containing no agglomerates having a size of 150 μm or more are judged to have good dispersity when they are observed with a light microscope.

Alternatively, the dispersity of the CNF dispersion may be evaluated by using the CNF dispersion index. The CNF dispersion index refers to an indicator of the dispersity of CNFs as a modification of the NEP index (e.g., disclosed in JPA No. 1996-134329), which is an indicator of the dispersity of fibers. Specifically, the CNF dispersion index is determined as follows:

1) Sandwich the dispersion between two glass plates to form a film having a thickness of 0.15 mm; observe the dispersion with a microscope to measure the major axes of agglomerates; and classify them as follows:
agglomerates having a size of 100 to 150 μm: large particles; agglomerates having a size of 50 to 100 μm: medium-sized particles; agglomerates having a size of 20 to 50 μm: small particles.

2) Calculate the CNF dispersion index by the equation below:

$$\text{CNF dispersion index} = (\text{the number of large particles} \times 64 + \text{the number of medium-sized particles} \times 8 + \text{the number of small particles} \times 1) \div 2.$$

3) Evaluate as follows:
Dispersions having a CNF dispersion index of 500 or less: good dispersity;
Dispersions having a CNF dispersion index of 100 or less: very good dispersity.

CNF redispersions evaluated to have good dispersity in dispersion media according to the present invention not only show high solubility in applications for foods, cosmetics, chemical products and the like but also contain little undispersed materials, thereby providing smooth touch and improving the mouth feel when they are added to foods or the like. Thus, transparency, light transmittance, reproducibility of viscosity and the like are improved if the CNFs are used in liquid products such as cosmetics, and on the other hand, transparency, light transmittance and the like are improved if they are used in chemical products such as optical films.

Foods according to the present invention contain the CNF dispersion or CNFs from the dispersion. Such foods include desserts and snacks such as flour-based baked foods (e.g., biscuits, crackers, etc.), Japanese rice crackers (including those made from non-glutinous rice called senbei, those made from glutinous rice called okaki, bite-sized crackers made from glutinous rice called arare, etc.), sweet buns (e.g., rusks, etc.), fried dough foods (including a traditional Japanese sweet and deep-fried snack food called karinto, etc.), chocolates, pastries and desserts, candies and caramels, higashi (i.e., a general term for traditional Japanese dry confectionery), uchigashi (i.e., a type of higashi made from rice or other cereal flour and sugar pressed in wood molds), mamegashi (i.e., traditional Japanese bean snacks), and yokan (i.e., a bar of gelled sweet bean paste); and manju (i.e., traditional Japanese steamed buns with sweet paste fillings), breakfast cereals, snacks, and dough products such as breads and noodles. The foods according to the present invention are preferably obtained by adding CNFs and optional ingredients such as sugar, oils and fats, eggs, dairy products, leavening agents, common salt, emulsifiers, flavorings and the like to a flour of a cereal such as wheat, corn, rye, oat, or rice to prepare a dough, which is then subjected to kneading and baking steps or subjected to kneading, fermentation and baking steps to prepare a food containing the flour as the primary ingredient such as biscuits, cookies, crackers, wafers, snacks, breakfast cereals, breads, as well as Japanese rice crackers such as senbei (made from non-glutinous rice), okaki (made from glutinous rice), arare (bite-sized crackers made from glutinous rice) and the like. It should be noted that baking also includes frying with oil.

Cosmetics according to the present invention contain the CNF dispersion or CNFs from the dispersion. Such cosmetics include skin care products such as creams, milky lotions, toners, and serums; personal cleansing products such as soaps, facial cleansers, shampoos, and rinses; hair care products such as hair tonics, and hairstyling products; makeup products such as foundations, eye liners, mascaras, and lipsticks; oral care products such as toothpastes; bath products; etc.

Rubber compositions according to the present invention contain the CNF dispersion or CNFs from the dispersion. Rubbers in the rubber compositions are typically based on organic polymers and have a high elastic limit and a low elastic modulus. Rubbers are mainly classified into natural rubbers and synthetic rubbers, and either may be used or both may be combined in the present invention. Natural rubbers may be natural rubbers in the narrow sense that have not been chemically modified, or may be chemically modified natural rubbers such as chlorinated natural rubbers, chlorosulfonated natural rubbers, epoxylated natural rubbers, hydrogenated natural rubbers, deproteinized natural rubbers and the like. Synthetic rubbers include, for example, diene rubbers such as butadiene rubbers (BR), styrene-butadiene copolymer rubbers (SBR), isoprene rubbers (IR), butyl rubbers (IIR), acrylonitrile-butadiene rubbers (NBR), chloroprene rubbers (CR), styrene-isoprene copolymer rubbers, styrene-isoprene-butadiene copolymer rubbers, isoprene-butadiene copolymer rubbers and the like; as well as ethylene-propylene rubbers (EPM, EPDM), acrylic rubbers (ACM), epichlorohydrin rubbers (CO, ECO), fluorinated rubbers (FKM), silicone rubbers (Q), urethane rubbers (U), and chlorosulfonated polyethylene (CSM).

EXAMPLES

<Preparation of a CNF Dispersion>

To 500 ml of an aqueous solution containing 39 mg of TEMPO (from Sigma Aldrich) and 514 mg of sodium bromide dissolved therein was added 5 g (on a bone dry basis) of an unbeaten softwood bleached kraft pulp (brightness 85%), and the mixture was stirred until the pulp was homogeneously dispersed. An aqueous sodium hypochlorite solution was added to the reaction system in an amount of 5.5 mmol/g to start an oxidation reaction. During the reaction, the pH in the system decreased, and therefore, a 3M aqueous sodium hydroxide solution was added as appropriate to adjust the reaction system to pH 10. The reaction was terminated when sodium hypochlorite has been consumed and the pH in the system became constant. After the reaction, the mixture was filtered through a glass filter to separate the pulp, and the pulp was thoroughly washed with water to give an oxidized pulp (carboxylated cellulose). The pulp yield was 90%, the time required for the oxidation reaction was 90 minutes, and the carboxyl group content was 1.6 mmol/g.

The oxidized pulp obtained in the process described above was adjusted to 1.0% (w/v) (=1.0% by mass) with water, and treated in a ultra-high pressure homogenizer (20° C., 150 Mpa) for three cycles to give an anionically modified cellulose nanofiber dispersion. The resulting fibers had an average fiber diameter of 40 nm and an aspect ratio of 150.

(Determination method of the carboxyl group content) The carboxylated cellulose was prepared into 60 ml of a 0.5% by mass slurry (aqueous dispersion) and adjusted to pH 2.5 by adding a 0.1M aqueous hydrochloric acid solution, and then a 0.05N aqueous sodium hydroxide solution was added dropwise while the electric conductivity was measured until the pH reached 11. The carboxyl group content was calculated from the amount of sodium hydroxide (a) consumed during the neutralization stage of the weak acid characterized by a moderate change in electric conductivity using the equation below:

Carboxyl group content [mmol/g carboxylated cellulose]=$a$[ml]×0.05/mass [g] of carboxylated cellulose.

(Determination Methods of the Average Fiber Diameter and Aspect Ratio)

The average fiber diameter and average fiber length of the anionically modified CNFs were analyzed on randomly chosen 200 fibers using a field emission scanning electron microscope (FE-SEM). The aspect ratio was calculated by the equation below:

Aspect ratio=average fiber length/average fiber diameter.

Example 1

The carboxylated CNFs described above (having a carboxyl group content of 1.6 mmol/g, an average fiber diameter of 40 nm and an aspect ratio of 150) were used as CNFs. To 1 g of a 1.0% by mass aqueous suspension of the CNFs were added two drops of Bokuteki (a brand name for a predispersed liquid sumi ink for brush calligraphy and paintings having a solids content of 10% available from Kuretake Co., Ltd.), and the suspension was stirred in a vortex mixer for 1 minute. Using Zetasizer Nano ZS (from Malvern), the average particle size of the liquid sumi ink was measured three times to be, on average, 0.22 μm. The dispersion was observed with a light microscope (the digital microscope KH-8700 (from HIROX Co., Ltd.)) at a magnification of 100×. The results are shown in FIG. 1. The CNF dispersion index was 0.

Example 2

Figure 2:
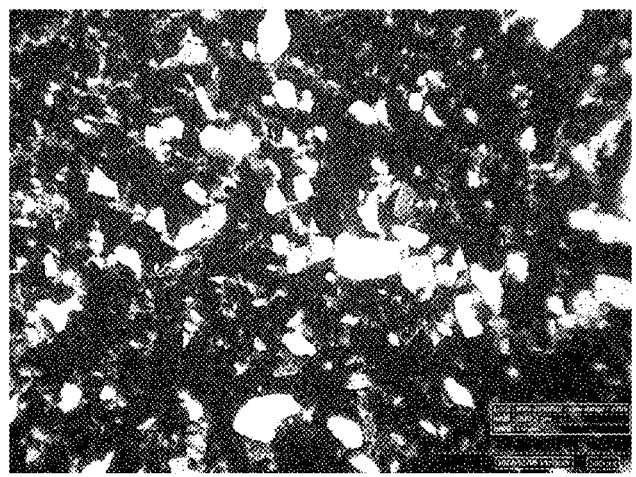
FIG. 2 shows an image of the CNF dispersion in Example 2 observed with a light micro scope.

The CNFs used in Example 1 were dried in a forced air drying oven at 105° C., and water was added again to prepare an aqueous CNF dispersion (having a solids content of 1.0% by mass), which was stirred by using T.K. HOMO MIXER (6,000 rpm) for 60 minutes. To the dispersion were added two drops of Bokuteki and the dispersion was stirred in a vortex mixer for 1 minute in the same manner as in Example 1. The dispersion was observed with a light microscope. The results are shown in FIG. 2. The CNF dispersion index was 1825.

Example 3

To 500 ml of an aqueous solution containing 39 mg of TEMPO (from Sigma Aldrich) and 514 mg of sodium bromide dissolved therein was added 5 g (on a bone dry basis) of an unbeaten softwood bleached kraft pulp (brightness 85%), and the mixture was stirred until the pulp was homogeneously dispersed. An aqueous sodium hypochlorite solution was added to the reaction system in an amount of 5.7 mmol/g to start an oxidation reaction. During the reaction, the pH in the system decreased, and therefore, a 3M aqueous sodium hydroxide solution was added as appropriate to adjust the reaction system to pH 10. The reaction was terminated when sodium hypochlorite has been consumed and the pH in the system became constant. After the reaction, the mixture was filtered through a glass filter to separate the pulp, and the pulp was thoroughly washed with water to give an oxidized pulp (carboxylated cellulose). The pulp yield was 90%, the time required for the oxidation reaction was 90 minutes, and the carboxyl group content was 1.67 mmol/g.

The oxidized pulp obtained in the process described above was adjusted to 1.0% (w/v) (=1.0% by mass) with water, and treated in a ultra-high pressure homogenizer (20° C., 150 Mpa) for five cycles to give an anionically modified cellulose nanofiber dispersion. The resulting fibers had an average fiber diameter of 4 nm and an aspect ratio of 150.

Figure 3:
FIG. 3 shows an image of the CNF dispersion in Example 3 observed with a light micro scope.

The same experiment as described in Example 2 was performed except that the CNFs thus obtained were dried in a forced air drying oven at 105° C., and water was added again as well as 40 parts of carboxymethyl cellulose per 100 parts by weight of the bone dry solids of the CNFs to prepare an aqueous CNF dispersion (having a solids content of 1.0% by mass), and the dispersion was observed with a light microscope. The results are shown in FIG. 3. The CNF dispersion index was 24.

Example 4

Figure 4:
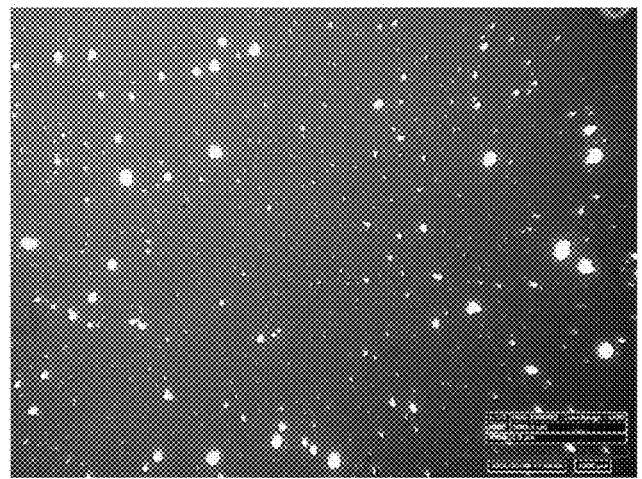
FIG. 4 shows an image of the CNF dispersion in Example 4 observed with a light micro scope.

The CNFs used in Example 3 were dried in a forced air drying oven at 105° C., and water was added again as well as 40 parts of carboxymethyl cellulose per 100 parts by weight of the bone dry solids of the CNFs to prepare an aqueous CNF dispersion (having a solids content of 1.0% by mass), which was stirred by using T.K. HOMO MIXER (1,000 rpm) for 60 minutes. To the dispersion were added two drops of Bokuteki and the dispersion was stirred in a vortex mixer for 1 minute in the same manner as in Example 1. The dispersion was observed with a light microscope. The results are shown in FIG. 4. The CNF dispersion index was 252.

Example 5

Figure 5:
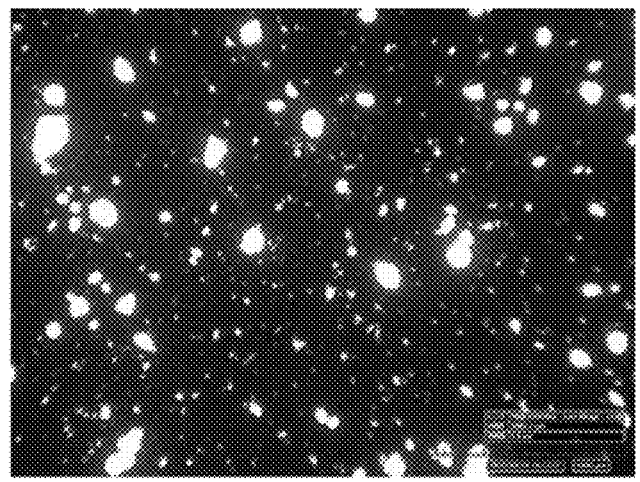
FIG. 5 shows an image of the CNF dispersion in Example 5 observed with a light micro scope.

The CNFs used in Example 3 were dried in a forced air drying oven at 105° C., and water was added again as well as 40 parts of carboxymethyl cellulose per 100 parts by weight of the bone dry solids of the CNFs to prepare an aqueous CNF dispersion (having a solids content of 1.0% by mass), which was stirred by using T.K. HOMO MIXER (600 rpm) for 180 minutes. To the dispersion were added two drops of Bokuteki and the dispersion was stirred in a vortex mixer for 1 minute in the same manner as in Example 1. The dispersion was observed with a light microscope. The results are shown in FIG. 5. The CNF dispersion index was 942.

Example 6

A dispersion was prepare by the same procedure as described in Example 1 except that the liquid sumi ink used was changed from Bokuteki (from Kuretake Co., Ltd.) to another commercially available predispersed liquid sumi ink (from KAIMEI & Co., Ltd.), and the dispersion was observed with a light microscope. As a result, it could be confirmed that no agglomerates were contained in the CNF dispersion. Using Zetasizer Nano ZS (from Malvern), the average particle size of the liquid sumi ink was measured three times to be, on average, 0.09 μm.

Example 7

A dispersion was prepare by the same procedure as described in Example 1 except that the liquid sumi ink used was changed to a liquid sumi ink obtained by grinding an inkstick (from Kuretake Co., Ltd.) against an inkstone with water, and the dispersion was observed with a light microscope. As a result, it could be confirmed that no agglomerates were contained in the CNF dispersion. Using Zetasizer Nano ZS (from Malvern), the average particle size of the liquid sumi ink was measured three times to be, on average, 0.51 μm.

Example 8

A dispersion was prepare by the same procedure as described in Example 1 except that the liquid sumi ink used was changed to an "aqueous pigment ink" prepared according to the process described in "Example 1" of JPA No. 2015-199966, and the dispersion was observed with a light microscope. As a result, it could be confirmed that no agglomerates were contained in the CNF dispersion.

Comparative Example 1

Figure 6:
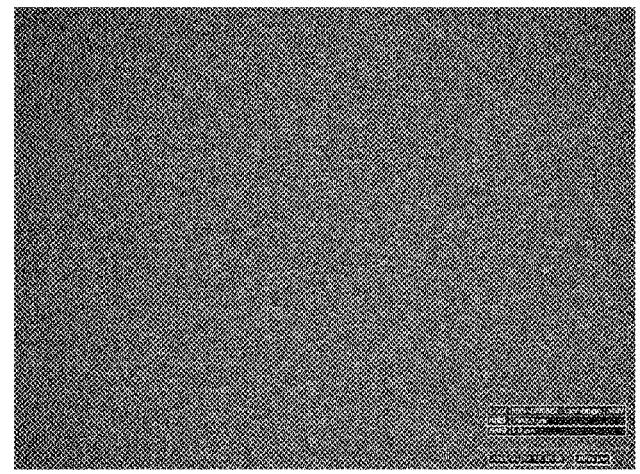
FIG. 6 shows an image of the CNF dispersion in Comparative example 1 observed with a light microscope.

The CNFs used in Example 1 were observed with a light microscope without adding any drops of liquid sumi ink. The results are shown in FIG. 6. The CNF dispersion index was 0.

Comparative Example 2

Figure 7:
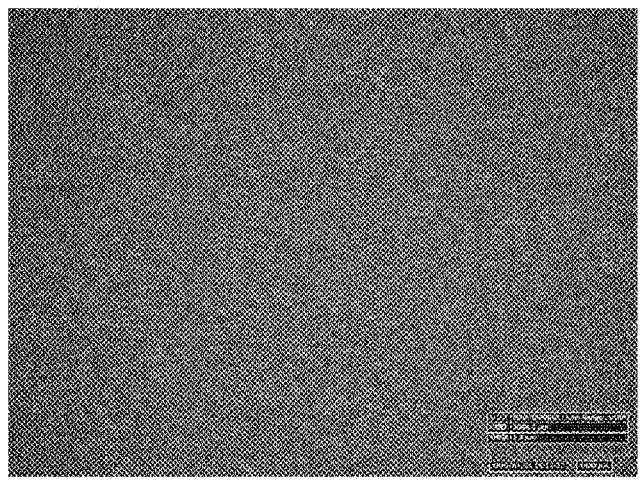
FIG. 7 shows an image of the CNF dispersion in Comparative example 2 observed with a light microscope.

The CNFs used in Example 2 were observed with a light microscope without adding any drop of liquid sumi ink. The results are shown in FIG. 7. The CNF dispersion index was 0.

<Results>

Observation results from the CNF dispersions having undergone no drying step and containing no agglomerates (FIGS. 1 and 6) showed no difference depending on whether or not a liquid sumi ink exists, but observation results from the CNF dispersions having undergone a drying step and containing agglomerates (FIGS. 2 to 5, and 7) showed a difference depending on whether or not a liquid sumi ink exists. These results demonstrated that whether or not agglomerates exist in CNF dispersions can be easily determined by observing the CNF dispersions to which a liquid sumi ink has been added with a light microscope, though it had been previously difficult to determine.

The invention claimed is:

1. A method for evaluating whether or not agglomerates of cellulose nanofibers exist in a cellulose nanofiber dispersion, which cannot be visually determined, comprising the steps of:
    (1) preparing a cellulose nanofiber dispersion;
    (2) adding a color pigment into the cellulose nanofiber dispersion; and
    (3) observing the cellulose nanofiber dispersion to which the color pigment has been added with a light microscope to determine whether or not agglomerates of cellulose nanofibers exist in a cellulose nanofiber dispersion, which cannot be visually determined, wherein the colored pigment is less transparent to light during observation with a light microscope.

2. The method of claim 1, wherein the colored pigment has an average particle size of 10 μm or less.

3. The method of claim 1, wherein the step (2) comprises adding a dispersion of a colored pigment to the cellulose nanofiber dispersion.

4. The method of claim 1, further comprising the step of:
    (4) determining the cellulose nanofiber (CNF) dispersion index as follows:

1) sandwich the dispersion between two glass plates to form a film having a thickness of 0.15 mm; observe the film with a microscope to measure the major axes of agglomerates; and classify the agglomerates as follows:

agglomerates having a size of 100 to 150 μm: large particles; agglomerates having a size of 50 to 100 μm: medium-sized particles; agglomerates having a size of 20 to 50 μm: small particles; and 2) calculate the CNF dispersion index by the equation below:

CNF dispersion index=(the number of large particles× 64+the number of medium-sized particles×8+the number of small particles×1)÷ 2.

5. The method of claim 1, wherein the agglomerates of cellulose nanofibers in a cellulose nanofiber dispersion are identified as a bright field.

\* \* \* \* \*